United States Patent
Barone et al.

(10) Patent No.: US 11,547,531 B2
(45) Date of Patent: Jan. 10, 2023

(54) METHOD AND APPARATUS FOR GENERATING DENTAL DATA SUITABLE FOR MANUFACTURING A DENTAL ALIGNER

(71) Applicant: AIRNIVOL S.R.L., Navacchio di Cascina (IT)

(72) Inventors: Sandro Barone, Pisa (IT); Monica Bordegoni, Legnano (IT); Armando Razionale, Cascina (IT); Aurelio Montalto, Savona (IT)

(73) Assignee: AIRNIVOL S.R.L., Navacchio di Cascina (IT)

( * ) Notice: Subject to any disclaimer, the term of this patent is extended or adjusted under 35 U.S.C. 154(b) by 386 days.

(21) Appl. No.: 16/750,869

(22) Filed: Jan. 23, 2020

(65) Prior Publication Data
US 2020/0237475 A1  Jul. 30, 2020

(30) Foreign Application Priority Data
Jan. 28, 2019 (IT) .......................... 102019000001203

(51) Int. Cl.
| | |
|---|---|
| *G06K 9/00* | (2022.01) |
| *A61C 7/00* | (2006.01) |
| *A61C 7/20* | (2006.01) |
| *A61C 7/08* | (2006.01) |

(Continued)

(52) U.S. Cl.
CPC .............. *A61C 7/002* (2013.01); *A61C 7/08* (2013.01); *A61C 7/20* (2013.01); *B33Y 50/00* (2014.12); *A61B 2576/00* (2013.01); *B33Y 80/00* (2014.12); *G06T 2207/30036* (2013.01)

(58) Field of Classification Search
CPC ...................................................... A61C 7/002
See application file for complete search history.

(56) References Cited

U.S. PATENT DOCUMENTS

| | | | |
|---|---|---|---|
| 6,493,415 B1 * | 12/2002 | Arai ......................... | A61B 6/14 378/38 |
| 7,373,286 B2 * | 5/2008 | Nikolskiy ............... | G06T 17/00 703/2 |
| 8,439,672 B2 | 5/2013 | Matov et al. | |

(Continued)

FOREIGN PATENT DOCUMENTS

WO    0180761 A2    11/2001

OTHER PUBLICATIONS

Adel; "Tip, Torque Rotations: How accurately do digital superimposition software packages quantify tooth movement"; Progress in Orthodontics; 2022; https://progressinorthodontics.springeropen.com/articles/10.1186/s40510-022-00402-x.

*Primary Examiner* — Oneal R Mistry
(74) *Attorney, Agent, or Firm* — Dickinson Wright PLLC; Andrew D. Dorisio

(57) ABSTRACT

The method for generating dental data suitable for manufacturing of a dental aligner, includes storing 3D scan data of a dental arch, determining (140) a curve in an occlusal plane, determining a positioning of the nodes of the teeth of the dental arch on the curve, determining an elevation of the nodes of the teeth of the dental arch, and determining an orientation of the teeth of the dental arch; said manufacturing data are calculated at least on the basis of the 3D scan data as well as the determined positioning, the determined elevation, and the determined orientation.

16 Claims, 7 Drawing Sheets

(51) Int. Cl.
    *B33Y 50/00*     (2015.01)
    *B33Y 80/00*     (2015.01)

(56) References Cited

U.S. PATENT DOCUMENTS

| | | | |
|---|---|---|---|
| 2006/0263741 A1 | 11/2006 | Imgrund et al. | |
| 2008/0232540 A1* | 9/2008 | Yoshimura | A61B 6/469 |
| | | | 378/4 |
| 2019/0053775 A1* | 2/2019 | Arai | A61B 6/501 |
| 2019/0328486 A1* | 10/2019 | Wealleans | A61C 5/44 |
| 2019/0350680 A1* | 11/2019 | Chekh | G06T 19/006 |
| 2020/0005550 A1* | 1/2020 | Schneider | A61C 13/34 |
| 2020/0085548 A1* | 3/2020 | Reynard | A61B 6/032 |

\* cited by examiner

METHOD AND APPARATUS FOR GENERATING DENTAL DATA SUITABLE FOR MANUFACTURING A DENTAL ALIGNER

FIELD OF THE INVENTION

This disclosure relates to a method and an apparatus for generating dental data suitable for manufacturing of a dental aligner.

BACKGROUND

With the advent of digital orthodontics, the virtual planning step of the orthodontic treatment has become fundamental to make it as reliable and predictable as possible.

In general, the design of orthodontic treatments can be developed directly or backwards.

In the first case (direct mode), tooth movements leading from the initial configuration of the teeth to the final configuration of the teeth are planned.

In the second case (reverse mode), the final configuration of the teeth is identified and the movements of the teeth necessary to obtain this final configuration are established.

Typically, the movements from the initial configuration to the final configuration are divided into steps; for example, one can decide that each step has a certain predetermined extent or has a certain maximum extent.

Such desired movements of the teeth are accomplished by the use of one or more "dental aligners"; the shape of the aligners depends on the movements themselves.

Determining the final "ideal" configuration of the teeth is complex since the medical and aesthetic canons underlying this determination are difficult to interpret and combine; in fact, if used poorly, they can give mediocre results and far from optimal.

SUMMARY

The disclosure has the general object of providing a methodology for automatically and univocally determining an "ideal" final configuration of the teeth starting from an initial configuration, which is actually obtainable by means of dental aligners.

This general object and other objects are achieved thanks to what is expressed in the appended claims that form an integral part of the present description.

A first aspect of the disclosure is a method for generating dental data suitable for manufacturing of a dental aligner.

A second aspect of the disclosure is an apparatus for manufacturing a dental aligner.

BRIEF DESCRIPTION OF THE DRAWING FIGURES

The disclosed concepts will become clearer from the following detailed description to be considered in conjunction with the accompanying drawings, in which.

Figure 1:
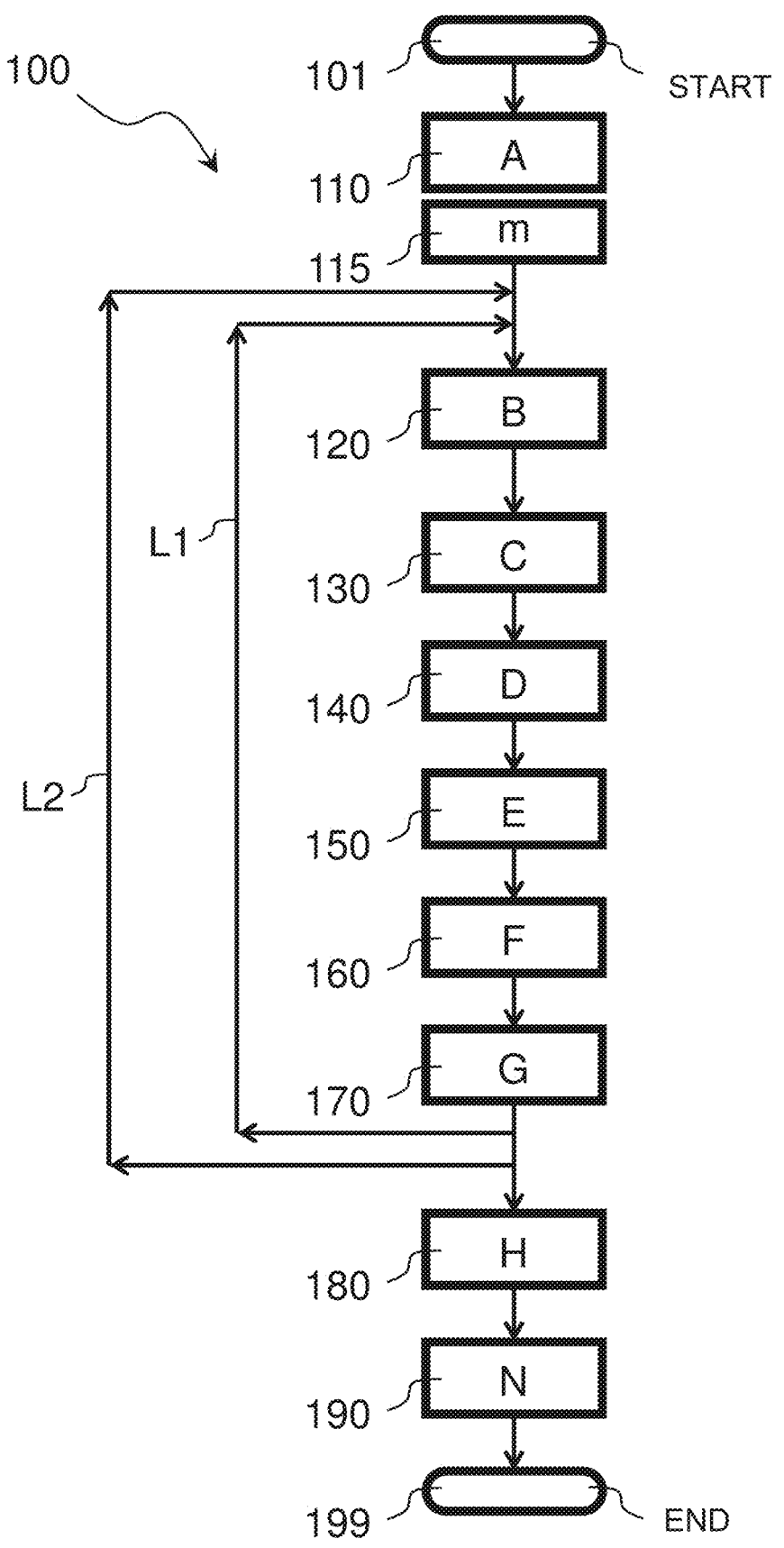
FIG. 1 shows a flowchart of an example of embodiment of the method according one aspect of the disclosure.

As can be easily understood, there are various ways of practically implementing the disclosed concepts, which are defined in its main advantageous aspects in the appended claims and not limited either to the following detailed description or to the appended claims.

DETAILED DESCRIPTION

The method according to the disclosure assumes to have previously carried out a 3D scan of a patient's dental arch to be subjected to an orthodontic treatment and, more typically, a 3D scan of the patient's upper dental arch and a 3D scan of the lower dental arch of the patient. In practice, an impression of a dental arch or a reproduction of a dental arch or an original of a dental arch (i.e. a direct scan of the patient's mouth) can be scanned. It should be noted that the scanning operation can be carried out in a place different from the place where the operations according to the disclosure are carried out, and/or that the scanning operation can be carried out by an apparatus different from the apparatus which performs the operations.

The preliminary scan operation is used to obtain the "initial" configuration of the patient's teeth.

Next, it is necessary to determine the desired "final" configuration of the patient's teeth; the "final" configuration determined according to the disclosure is considered "ideal" for the patient.

For this purpose, according to the disclosure (consider the flow chart of FIG. 1 as a support), at least the following steps are provided:

A) storing (block 110 in FIG. 1) the 3D scan obtaining scan data from at least one dental arch, m) possibly segmenting (block 115 in FIG. 1) the scan data so that each block of data corresponds to a distinct tooth of the dental arch, B) for each tooth of a dental hemiarch of the dental arch, calculating (block 120 in FIG. 1) position of a node, width, inclination of a disto-mesial axis, inclination of a root axis, and inclination of a linguo-buccal axis starting from the scan data (or from the corresponding block of scan data), C) selecting (block 130 in FIG. 1) at least a first node referred to in the calculation of step B, D) determining (block 140 in FIG. 1) a curve (see for example FIG. 8) in an occlusal plane that passes at least through the first node (detailed explanations follow), E) determining (block 150 in FIG. 1) a positioning of the nodes of the teeth of the dental hemiarch on this curve or a similar curve, for example an "adjusted" or "adapted" curve (detailed explanations follow), F) determining (block 160 in FIG. 1) an elevation of the nodes of the teeth of the dental hemiarch (detailed explanations follow), and G) determining (block 170 in FIG. 1) an orientation of the teeth of the dental hemiarch (detailed explanations follow).

Typically, steps "B"-"G" will be repeated for both dental hemiarches of the dental arch. Optionally and advantageously, a step "H" may also be provided (block 180 in FIG. 1) to determine a relative positioning of the teeth of the patient's upper arch and of the teeth of the patient's lower arch; typically, the step "H" is carried out after performing the steps "B"-"G" for both dental arches.

Finally, the dental data suitable for manufacturing of one or more dental aligners can be calculated, i.e. a final step "N" is carried out (block 190 in FIG. 1).

For completeness, it should be noted that the diagram presents a beginning of the flow, i.e. of the process, represented by block 101 and an end of the flow, i.e. of the process, represented by block 199.

These dental manufacturing data are calculated on the basis of the "initial" configuration and the "final" configuration, or rather on the basis of the difference between the "final" configuration and the "initial" configuration, and can be calculated according to one of the known techniques. For example, the difference between the "final" configuration and the "initial" configuration can be seen as a composition of small displacements each associated with a single aligner within the treatment (see U.S. Pat. No. 8,439,672).

In the case of the disclosure, the dental manufacturing data depend at least on the scan data ("initial configuration") as well as on the positioning determined in step "E", on the elevation determined in step "F", on the orientation determined in step "G" and, possibly, on the relative positioning determined in step "H" ("final configuration").

It should be noted that the order "B", "C", "D", "E", "F" and "G" indicated above needs not be followed strictly although being preferred; for example, instead of doing "E" then "F" then "G", one can do "E" then "G" then "F".

Figure 3:
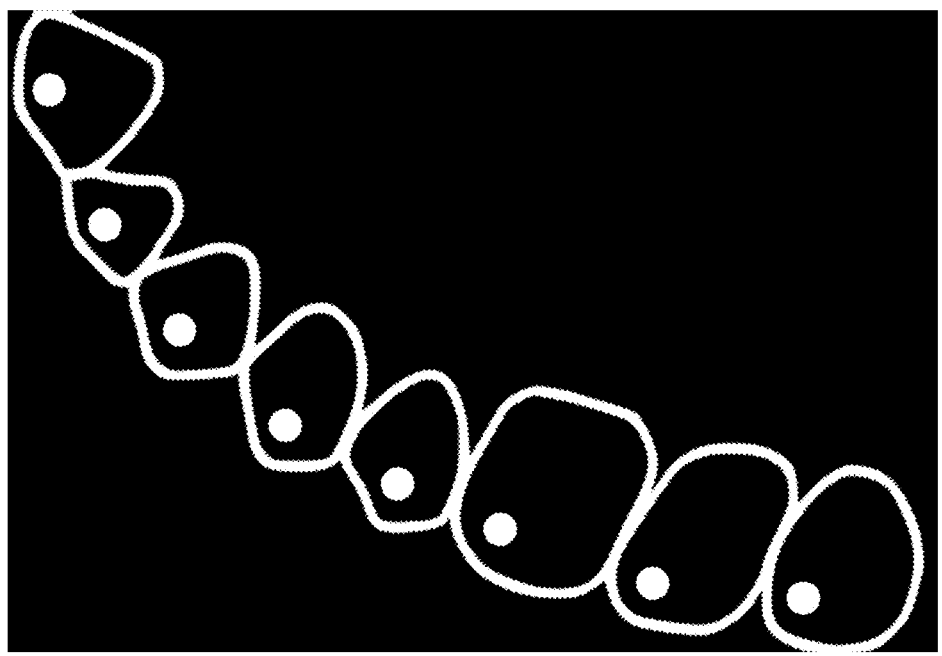
FIG. 3 shows a schematic top view of the teeth of a hemiarch and the related nodes.
Figure 5:
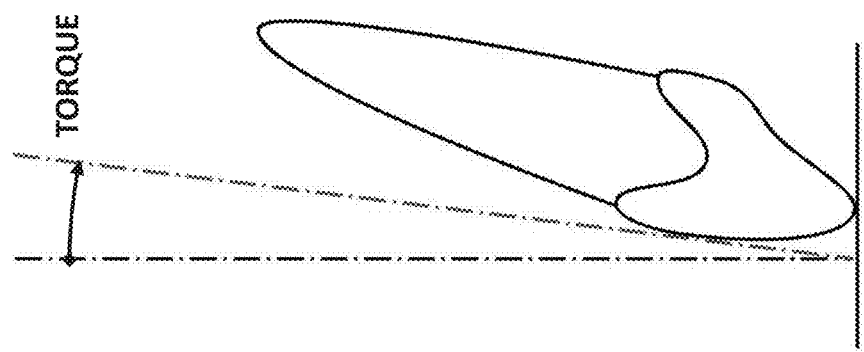
FIG. 5 shows a view of a tooth which allows understanding the TORQUE angle.

The above steps provide that a "node" or "main node" and a (local) reference system are defined for each tooth. The main node coincides with an anatomical point always identifiable on each tooth; for example: for the incisors this node coincides with the midpoint of the incisal margin; for canines with the only cusp present; for the premolars with the buccal cusp; for molars with the mesio-buccal cusp (see for example in FIG. 3 the teeth of a hemiarch and its nodes). The local reference system is typically arranged according to these rules: origin in the main node, first axis (or X axis) in the direction and towards the linear regression of the distal-mesial sulcus or, for the incisors, or the linear regression of the incisal margin, second axis (or Y axis) orthogonal to the first axis and in the direction and towards the root apex, third axis (or Z axis) arranged to form a right-hand XYZ triad with the first and second axes.

Furthermore, for each tooth, a width is defined, i.e. an extension in the direction of the first axis, and a position of the node with respect to this width (it should be noted that the position of the node, therefore of the origin of the local reference, does not coincide in general with the centre line of the tooth); these parameters can be used advantageously in step "E".

In step "E", positioning typically derives, for each tooth of the hemiarch, from a combination of a translation of the tooth and a rotation of the tooth around the root axis; preferably, this positioning takes into account the actual width of the teeth.

Figure 9:
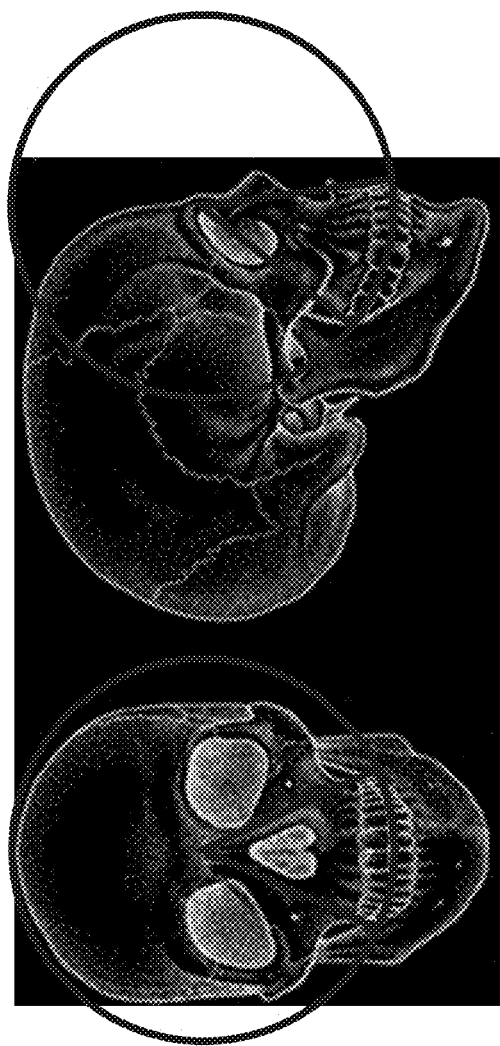
FIG. 9 shows a Monson sphere superimposed on a skull according to a front view and according to a side view.

In step "F", the elevation typically derives, for each tooth of the hemiarch, from a translation (in particular in the occlusal direction) of the tooth such that the node of the tooth is on a Monson sphere (see for example FIG. 9).

Figure 4:
FIG. 4 shows a view of a tooth which allows understanding the TIP angle.

In step "G", the orientation typically derives, for each tooth of the hemiarch, from a rotation of the tooth such that the TIP angle of the tooth (see for example FIG. 4) and the TORQUE angle of the tooth (see for example FIG. 4) correspond to predetermined angle values—one can think of using two tables in which the values of these angles are stored according to the type of tooth and, possibly, other factors; as can be seen for example in FIG. 9, the ideal configuration of the various teeth provides, in general, TIP angles and TORQUE angles different from zero and from each other; this rotation can correspond to the combination of a rotation to "adjust" the angle of TIP and a rotation to "adjust" the angle of TORQUE. A rotation is for example around the tooth Z axis or around an axis parallel to the Z axis passing through a point near the node for the teeth where the node is not central.

An important aspect of the disclosure is the determination of the curve in the occlusal plane corresponding to the step "F" indicated above.

In theory there could be many ways to determine it. According to the disclosure, one proceeds by considering one hemiarch at a time and it is assumed that at least two points, preferably three points, extrapolated from the "initial" configuration of the hemiarch are "ideal" or, at least, "acceptable"; if anything, four points could also be used. In the case of use of two points, the preferred possibilities are two: 1) a first point is a node of a tooth (for example the central incisor) and a second point is a node of another tooth (for example the first molar) relatively far from the first point, and 2) a first point is a central point of a dental interstice between two central incisors and a second point is a node of another tooth (for example the first molar) relatively far from the first point. In the case of use of three points, the preferred possibilities are two: 3) a first point is a node of a tooth (for example the central incisor) and a second point is a node of another tooth (for example the canine) relatively far from the first point and a third point is a node of an additional tooth (e.g. the first molar) relatively far from the second point, and 4) a first point is a central point of a dental interstice between two central incisors and a second point is a node of another tooth (e.g. the canine) relatively far from the first point and a third point is a node of a further tooth (e.g. the first molar) relatively far from the second point.

The choice of the number and position of the points can be made taking into consideration two specific needs: the first is to obtain an "optimal" length of the arches according to the width of the teeth, or to minimize any operations to reduce the width of the teeth and/or the presence of diastemas (space between two adjacent teeth); the second is to minimize the variation in the distances between the canines and the molars of each arch, to limit post-treatment recurrences.

A curve is then identified which passes through the two or three points considered. According to the possibilities "1" and "2", the curve can advantageously be a parabolic arch which passes through the two points and whose tangent in the first point preferably has a predetermined null or small value. According to the possibilities "3" and "4", the curve can advantageously be two sections of the curve, in particular of a parabola, connected or substantially connected in an intermediate position; the first section passes through the first point and the second point; the second section passes through the second point and the third point; the tangent in the first point of the first section preferably has a predetermined null or small value; the tangent in the second point of the second section preferably has the same value as the tangent in the second point of the first section.

Figure 8:
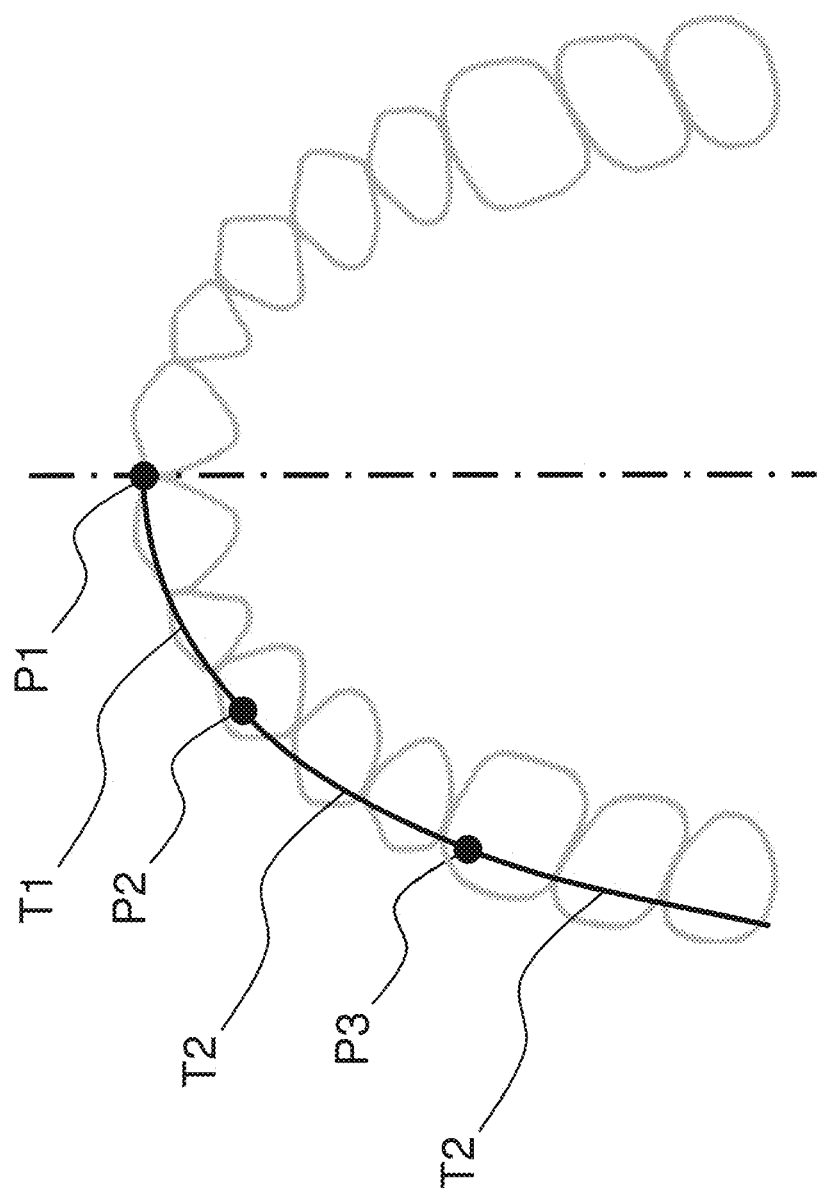
FIG. 8 shows a schematic top view of the teeth of a dental arch and of a curve determined by applying an example of embodiment of the method according to the disclosure to one of the two hemiarches of the dental arch.

FIG. 8 illustrates the possibility "4" which is very preferred; the first point is indicated with P1, the second point is indicated with "P2", the third point is indicated with "P3", the first parabola section is indicated with "T1", and the second parabola section is indicated with "T2".

Having taken great care in determining the curve at step "D", it is appropriate to have equal care also in step "E", i.e. in determining the displacement of the teeth. It has already been said that it is preferable that this displacement takes into account the actual width of the teeth. At this point it is worth adding that it is preferable that this displacement, in particular the rotation of the teeth around their root axis, is such that a distal-mesial axis of each tooth of the hemiarch is tangent to the determined curve.

Typically, the steps "B"-"G" are repeated (L1) for both the hemiarches of the same dental arch; in FIG. 1, this repetition is represented by the ring section L1; preferably, the same Monson sphere is used for both cycles.

Typically, the steps "B"-"G" are repeated for both the hemiarches of a first and a second dental arch of a patient; in FIG. 1, the repetition relating to the two arches is represented by the ring section L2; preferably, the same Monson sphere is used. It may happen that, for some patients, the use of the same sphere of Monson leads to excessively calculated repositionings for one or more teeth; in this case, manual adjustments of the calculated relocations possibly guided by an electronic computer can be provided.

As already mentioned, after step "G" (or rather after a step "G" carried out on the upper right hemiarch, a step "G" carried out on the upper left hemiarch, a step "G" carried out on the lower right hemiarch, a step "G" performed on the lower left hemiarch), there may be a step "H".

Figure 7:
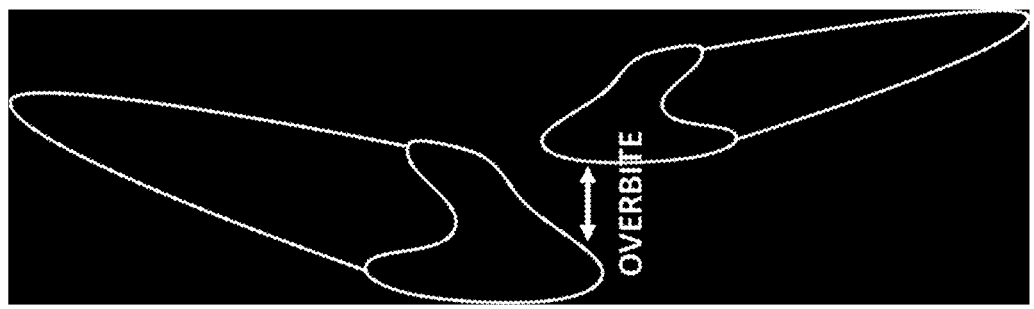
FIG. 7 shows a view of two teeth which allows understanding the OVERBITE parameter.
Figure 6:
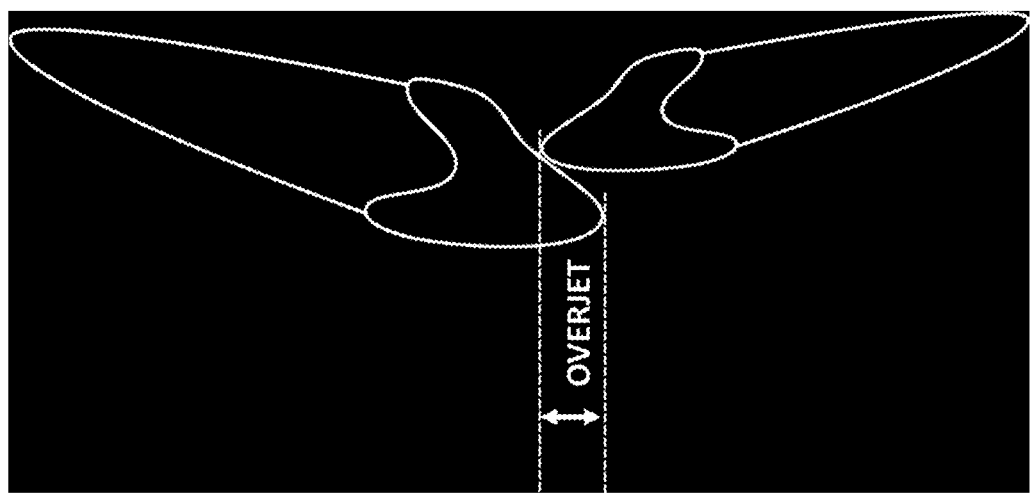
FIG. 6 shows a view of two teeth which allows understanding the OVERJET parameter.

In the step "H", the relative positioning typically derives from a translation of the teeth of the first dental arch (after they have been positioned and elevated and oriented) with respect to the teeth of the second dental arch (after they have been positioned and elevated and oriented) such that a value of an OVERJET parameter (see for example FIG. 6) and a value of an OVERBITE parameter (see for example FIG. 7) fall into ranges of predetermined values.

It should be noted that, for some patients, the step "H" may "fail", i.e. that it is not possible to find a relative positioning such that the value of the OVERJET parameter and the value of the OVERBITE parameter fall within predetermined ranges of values. In this case, for example, manual adjustments may be appropriate, possibly guided by an electronic computer, perhaps to take into account the "dental class" or "orthodontic class".

It is not excluded that calculations for all the teeth of a patient's mouth can be performed in an order other than step-A→step-G (for a first hemiarch), step-A→step-G (for a second hemiarch), step-A→step-G (for a third hemiarch), step-A→step-G (for a fourth hemiarch); this allows, for example, using the results of some steps on a hemiarch or arch for another step on another hemiarch or arch. A practical application of this concept is the generation of dental data suitable for manufacturing of dental aligners also aimed at correcting the "dental class" or "orthodontic class".

In general, it may be advantageous that the dental data deriving from the automatic processing described above are subjected to manual adjustments possibly guided by an electronic processor.

According to the exemplary embodiment of FIG. 1, the "ideal" configurations of the teeth of the four arches are determined one independently of the other.

However, the disclosure does not exclude that such determinations may take into account constraints between them.

For example, one could impose that the curve referred to in step "E" is exactly the same (but mirrored) for both the right and the left hemiarch. In this case, one could, for example, determine the curve according to step D for the right hemiarch, determine the curve according to step D for the left hemiarch, and then choose one of the two or combine them in some way (in particular average curve); therefore, a further "adjustment" or "adaptation" step of the curve may be provided between step D and step E and, obviously, positioning the teeth of each of the hemiarches on the "adjusted" or "adapted" curve.

Figure 2:
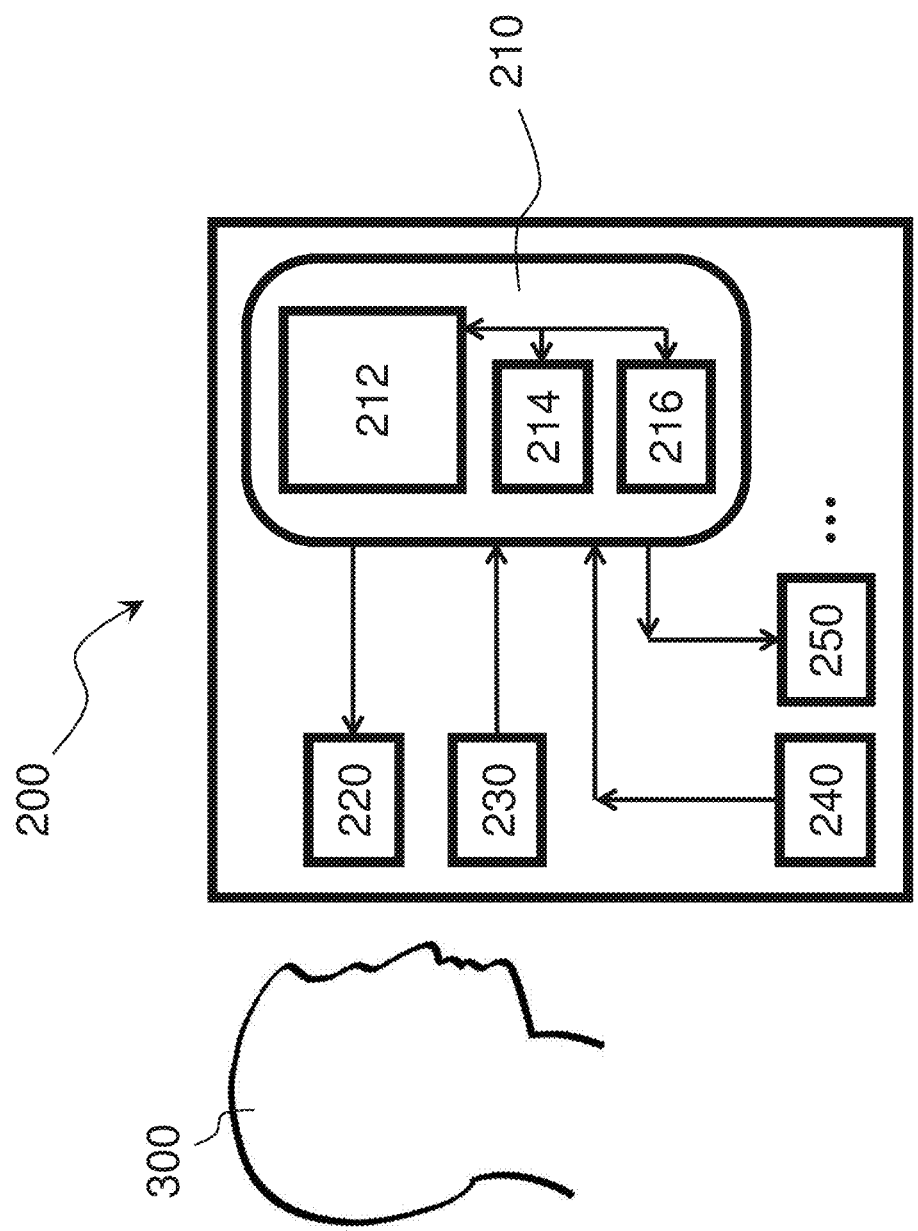
FIG. 2 shows a block diagram of an example of embodiment of the apparatus according to another aspect of the disclosure.

The methods according to the disclosure can be implemented for example through the apparatus 200 of FIG. 2.

The apparatus 200 comprises an electronic unit 210 of the computerized type, which in turn comprises a processor 212 and a program memory 214 and a data memory 216, one or more output interface devices 220 (connected to the unit 210) to transmit information to a user 300, and one or more input interface devices 230 (connected to the unit 210) to receive information and/or commands from the user 300.

Memory 214 will store portions of code suitable to allow implementing at least steps B-G of the method according to the disclosure, but typically also portions of code for steps A and/or H.

Scan data will typically be stored in memory 216, as well as intermediate and final results of the processing of the disclosed method.

The apparatus 200 further comprises a scanner 240 (connected to the unit 210) suitable for carrying out a 3D scan of an impression of a dental arch or a reproduction of a dental arch or an original of a dental arch and for generating scan data of the dental arch, such as a 3D scanner; the scanner 240 is adapted to send dental arch scan data to the unit 210.

The apparatus 200 further comprises a manufacturing arrangement 250 (connected to the unit 210) suitable for carrying out at least one manufacturing step of a dental aligner based on the calculated dental data. The manufacturing arrangement 250 is adapted to receive from the unit 210 manufacturing commands according to the manufacturing data generated by the disclosed method. The term "manufacturing arrangement" is intended to mean any combination of one or more additive manufacturing machines and/or subtractive manufacturing machines. An "additive manufacturing machine" is for example a 3D printer. A "subtractive manufacturing machine" is for example a grinder or a cutter or a drill.

The invention claimed is:

1. A method for generating dental data suitable for manufacturing of a dental aligner, comprising the steps of:
   A) storing a 3D scan of an impression of a dental arch or of a reproduction of a dental arch or of an original of a dental arch, obtaining scan data of said dental arch,
   B) for each tooth of a dental hemiarch of said dental arch, calculate position of a node, width, inclination of a disto-mesial axis, inclination of a root axis, and inclination of a linguo-buccal axis from said scan data,
   C) selecting at least one node according to the calculation of step B,
   D) determining a curve in an occlusal plane passing through said at least one node,
   E) determining a positioning of the nodes of said dental hemiarch on said curve, in which said positioning derives, for each tooth of said dental hemiarch, from a combination of a tooth translation and a tooth rotation around to the root axis, where said positioning takes into account the width of the teeth,
   F) determining an elevation of the nodes of each tooth of said dental hemiarch, wherein said elevation derives, for each tooth of said hemiarch, from a translation of the tooth such that the tooth node is on a sphere of Monson, and G) determining an orientation of each tooth of said dental hemiarch, wherein said orientation derives, for each tooth of said dental hemiarch, from a rotation of the tooth such that the TIP angle and the TORQUE angle of the tooth correspond to predetermined angle values;

whereby said dental data are calculated on the basis of said scan data as well as the positioning determined in step E, the elevation determined in step F, the orientation determined in step G.

2. Method according to claim 1, wherein in step B:
a node of an incisor tooth corresponds to the midpoint of the incisal margin, or
a node of a canine tooth corresponds to the cusp or
a node of a premolar tooth corresponds to the buccal cusp, or
a node of a molar tooth corresponds to the mesio-buccal cusp.

3. Method according to claim 1, in which step C comprises selecting only one canine tooth node and a node of the first molar tooth.

4. Method according to claim 1, wherein in phase said curve corresponds to the union of a first curve section, in particular of a parabola, and a second curve section, in particular of a parabola.

5. Method according to claim 4, wherein said first portion of the parabola joins said midpoint of a dental interstitium between two front incisor teeth of said dental arch and said canine tooth node, wherein said second section of parabola joins said node of the canine tooth and said node of the first molar tooth and proceeds further.

6. Method according to claim 1, wherein in phase E the positioning is such that a disto-mesial axis of each tooth of said dental hemiarch is tangent to said curve.

7. Method according to claim 1, wherein phases B-G are repeated for both dental hemiarches of said dental arch.

8. Method according to claim 7, wherein phases B-G are repeated for both the hemiarches of a first and a second dental arches of a person.

9. Method according to claim 8, comprising, after phase G, a phase H for determining a relative positioning wherein said relative positioning derives from a translation of the teeth of said first dental arch with respect to the teeth of said second dental arch such that a value of an OVERJET parameter and a value of an OVERBITE parameter fall in predetermined ranges of values, and whereby said dental data are calculated on the basis of said scan data as well as the positioning determined in step E, the elevation determined in step F, the orientation determined in step G, to the relative positioning determined in phase H.

10. Method according to claim 1, wherein said dental data are subject to manual adjustments guided by an electronic computer.

11. Apparatus for manufacturing a dental aligner, comprising an electronic unit adapted to carry out the method according to claim 1.

12. Apparatus according to claim 11, wherein said electronic unit is of the computerized type and comprises code portions adapted to enable at least the steps B-G.

13. Apparatus according to claim 11, comprising a scanner adapted to carry out a 3D scan of an impression of a dental arch or of a reproduction of a dental arch or of an original of a dental arch and to generate said scan data of said dental arch.

14. Apparatus according to claim 11, comprising a manufacturing arrangement adapted to realize at least one manufacturing step of a dental aligner on the basis of said calculated dental data.

15. A method for generating dental data suitable for manufacturing of a dental aligner, comprising the steps of:
A) storing a 3D scan of an impression of a dental arch or of a reproduction of a dental arch or of an original of a dental arch, obtaining scan data of said dental arch,
B) for each tooth of a dental hemiarch of said dental arch, calculate position of a node, width, inclination of a disto-mesial axis, inclination of a root axis, and inclination of a linguo-buccal axis from said scan data,
C) selecting at least two nodes according to the calculation of step B,
D) determining a curve in an occlusal plane passing through said at least two nodes,
E) determining a positioning of the at least two nodes of said dental hemiarch on said curve, in which said positioning derives, for each tooth of said dental hemiarch, from a combination of a tooth translation and a tooth rotation around to the root axis, where said positioning takes into account the width of the teeth,
F) determining an elevation of the at least two nodes of each tooth of said dental hemiarch, wherein said elevation derives, for each tooth of said hemiarch, from a translation of the tooth such that the tooth node is on a sphere of Monson, and
G) determining an orientation of each tooth of said dental hemiarch, wherein said orientation derives, for each tooth of said dental hemiarch, from a rotation of the tooth such that the TIP angle and the TORQUE angle of the tooth correspond to predetermined angle values;

whereby said dental data are calculated on the basis of said scan data as well as the positioning determined in step E, the elevation determined in step F, the orientation determined in step G.

16. A method for generating dental data suitable for manufacturing of a dental aligner, comprising the steps of:
A) storing a 3D scan of an impression of a dental arch or of a reproduction of a dental arch or of an original of a dental arch, obtaining scan data of said dental arch,
B) for each tooth of a dental hemiarch of said dental arch, calculate position of a node, width, inclination of a disto-mesial axis, inclination of a root axis, and inclination of a linguo-buccal axis from said scan data,
C) selecting at least two nodes according to the calculation of step B,
D) determining a curve in an occlusal plane passing through said at least two nodes,
E) determining a positioning of the at least two nodes of said dental hemiarch on said curve, in which said positioning derives, for each tooth of said dental hemiarch, from a combination of a tooth translation and a tooth rotation around to the root axis, where said positioning takes into account the width of the teeth,
F) determining an elevation of the at least two nodes of each tooth of said dental hemiarch, wherein said elevation derives, for each tooth of said hemiarch, from a translation of the tooth such that the tooth node is on a sphere of Monson, and
G) determining an orientation of each tooth of said dental hemiarch, wherein said orientation derives, for each tooth of said dental hemiarch, from a rotation of the tooth such that the a first characterizing angle feature and a second characterizing angle feature correspond to predetermined angle values;

whereby said dental data are calculated on the basis of said scan data as well as the positioning determined in step E, the elevation determined in step F, the orientation determined in step G.

\* \* \* \* \*